United States Patent
Ser et al.

(10) Patent No.: US 9,835,444 B2
(45) Date of Patent: Dec. 5, 2017

(54) SHAPE MEASURING DEVICE USING FREQUENCY SCANNING INTERFEROMETER

(71) Applicant: KOH YOUNG TECHNOLOGY INC., Seoul (KR)

(72) Inventors: Jang-Il Ser, Gyeonggi-do (KR); Hong-Ki Kim, Yongin-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 1 day.

(21) Appl. No.: 14/892,330

(22) PCT Filed: May 20, 2014

(86) PCT No.: PCT/KR2014/004490
§ 371 (c)(1),
(2) Date: Nov. 19, 2015

(87) PCT Pub. No.: WO2014/189252
PCT Pub. Date: Nov. 27, 2014

(65) Prior Publication Data
US 2016/0109227 A1    Apr. 21, 2016

(30) Foreign Application Priority Data

May 20, 2013    (KR) .................. 10-2013-0056523
May 20, 2014    (KR) .................. 10-2014-0060382

(51) Int. Cl.
*G01B 11/02*    (2006.01)
*G01B 11/24*    (2006.01)
(Continued)

(52) U.S. Cl.
CPC ............ *G01B 11/2441* (2013.01); *G01B 9/02* (2013.01); *G01B 9/02002* (2013.01);
(Continued)

(58) Field of Classification Search
CPC ............ G01B 11/2441; G01B 11/0608; G01B 11/0675; G01B 9/02; G01B 9/02002;
(Continued)

(56) References Cited

U.S. PATENT DOCUMENTS 5,064,291 A * 11/1991 Reiser .............. G01N 21/95684
348/131
5,495,424 A *  2/1996 Tokura ............. G01N 21/95684
348/129
(Continued)

FOREIGN PATENT DOCUMENTS

CN    102341669    2/2012
JP    8-159710     6/1996
(Continued)

OTHER PUBLICATIONS

International Search Report for International Application No. PCT/KR2014/004490, dated Sep. 4, 2014.
(Continued)

*Primary Examiner* — Tarifur Chowdhury
*Assistant Examiner* — Jonathon Cook
(74) *Attorney, Agent, or Firm* — Kile Park Reed & Houtteman PLLC

(57) ABSTRACT

A shape measuring device includes a light source unit, a light splitting unit, a reference mirror, a light receiving unit and a processing unit. The light source unit generates light and can change the wavelength of the light. The light splitting unit splits the light generated from the light source unit into at least a reference light and a measurement light. The light receiving unit receives the reference light which is reflected by the reference mirror so as to form a reference light path, and the measurement light which is reflected by a light-transmitting target object formed on a substrate so as to form a measurement light path. The processing unit
(Continued)

calculates the shape of the measurement argent object based on an interference change resulting from a wavelength change of the light between the reference light and the measurement light received by the light receiving unit.

6 Claims, 5 Drawing Sheets

(51) Int. Cl.
  *G01B 9/02* (2006.01)
  *G01B 11/06* (2006.01)
  *G01N 21/956* (2006.01)

(52) U.S. Cl.
  CPC ...... *G01B 11/0608* (2013.01); *G01B 2210/56* (2013.01); *G01N 2021/95646* (2013.01)

(58) Field of Classification Search
  CPC .............. G01B 9/0209; G01B 9/02024; G01B 9/02017; G01B 9/02019; G01B 2210/56; G01N 2021/95646; G01N 21/9501; H01L 22/12; G01M 11/005; G01M 11/025; G01M 11/0271; G01J 9/02
  USPC ........................................ 356/503, 513, 515
  See application file for complete search history.

(56) References Cited

U.S. PATENT DOCUMENTS

| | | | |
|---|---|---|---|
| 6,597,460 B2* | 7/2003 | Groot | G01B 11/30 356/497 |
| 9,221,128 B2* | 12/2015 | Jeong | B23K 31/125 |
| 2006/0262321 A1 | 11/2006 | De Groot | |
| 2010/0195113 A1 | 8/2010 | Lee et al. | |
| 2011/0122418 A1 | 5/2011 | Jansen | |
| 2011/0292375 A1* | 12/2011 | Marx | G01B 11/22 356/51 |
| 2012/0257207 A1* | 10/2012 | Marx | G01B 9/02004 356/451 |
| 2013/0038863 A1 | 2/2013 | Fresquet | |

FOREIGN PATENT DOCUMENTS

| | | |
|---|---|---|
| JP | 2003-534540 | 11/2003 |
| JP | 2006-349657 | 12/2006 |
| JP | 2009-115503 | 5/2009 |
| JP | 2011-107139 | 6/2011 |
| KR | 10-2010-0092058 | 8/2010 |
| KR | 10-2013-0015893 | 2/2013 |
| WO | 01/59402 | 8/2001 |
| WO | 01/90685 | 11/2001 |
| WO | 2009/079334 | 6/2009 |
| WO | 2010/011656 | 1/2010 |

OTHER PUBLICATIONS

Japanese Office Action with English Translation for Japanese Application No. 2016-515263, dated Nov. 1, 2016.

Chinese Office Action with English Translation for Chinese Application No. 201480001349.5, dated Nov. 3, 2016.

* cited by examiner

SHAPE MEASURING DEVICE USING FREQUENCY SCANNING INTERFEROMETER

TECHNICAL FIELD

The present disclosure relates to a shape measuring device and, more particularly, to a shape measuring device using a frequency scanning interferometer.

BACKGROUND ART

In general, at least one printed circuit board (PCB) is provided within an electronic device. Various circuit elements such as a circuit pattern, a connecting pad portion, and a drive chip electrically connected to the connecting pad portion are mounted on the printed circuit board.

Generally, a mounting substrate obtained by mounting electronic components on a printed circuit board (PCB) is used in a variety of electronic products. The mounting substrate is manufactured by soldering in a pad region of a substrate and bonding terminals of electronic components to a solder region.

A flux is often used in order to perform the soldering. It is necessary to form a suitable amount of flux in a desired position of a substrate. Thus, there is a demand for a measuring device and a measuring method for accurately measuring a three-dimensional shape of the flux.

SUMMARY

Embodiments of the present disclosure include a shape measuring device capable of effectively measuring a three-dimensional shape of a measurement target object, using a frequency scanning interferometer.

A shape measuring device according to one exemplary embodiment of the present disclosure includes a light source unit, a light splitting unit, a reference mirror, a light receiving unit and a processing unit. The light source unit is configured to generate light and to change a wavelength of the light. The light splitting unit is configured to split the light generated from the light source unit into at least a reference light and a measurement light. The reference mirror is configured to reflect the reference light. The light receiving unit is configured to receive the reference light reflected by the reference mirror so as to form a reference light path and the measurement light reflected by a light-transmitting measurement target object formed on a substrate so as to form a measurement light path. The processing unit is configured to calculate a shape of the measurement target object based on an interference change between the reference light and the measurement light received by the light receiving unit, which results from a wavelength change of the light, by calculating an absolute height of a first area of the measurement target object and a relative height of a second area of the measurement target object with respect to the first area and matching the absolute height of the first area and the relative height of the second area.

For example, the measurement target object may have a viscosity and may have a dot shape when viewed in a plan view. In this case, the first area may include a peak point of the measurement target object, and the second area may include a plurality of slant points in a slant surface positioned around the peak point.

In one embodiment, the substrate may include a base substrate, a non-conductive layer formed on the base substrate and provided with at least one hole, and a conductive layer formed thinner than the non-conductive layer and corresponding to the hole. The measurement target object may include a flux formed on at least the conductive layer. The flux formed on the conductive layer may be formed so as to fill at least a portion of the hole and may be formed so as to cover a portion of the non-conductive layer adjoining the hole.

In one embodiment, the processing unit may be configured to calculate the absolute height of the first area using a first light path difference between a light of the measurement light reflected directly at the first area of the measurement target object and the reference light and a second light path difference between a light of the measurement light transmitted through the first area of the measurement target object and then reflected at the conductive layer and the reference light.

In one embodiment, the processing unit may be configured to calculate the relative height of the second area using a third light path difference between a light of the measurement light transmitted through the second area of the measurement target object and then reflected at the conductive layer and the reference light.

A shape measuring device according to another exemplary embodiment of the present disclosure includes a light source unit, a light splitting unit, a reference mirror, a light receiving unit and a processing unit. The light source unit is configured to generate light and to change a wavelength of the light. The light splitting unit is configured to split the light generated from the light source unit into at least a reference light and a measurement light. The reference mirror is configured to reflect the reference light. The light receiving unit is configured to receive the reference light reflected by the reference mirror so as to form a reference light path and the measurement light reflected by a light-transmitting measurement target object formed on a surface of a specific material so as to form a measurement light path. The processing unit is configured to calculate a shape of the measurement target object based on an interference change between the reference light and the measurement light received by the light receiving unit, which results from a wavelength change of the light, by calculating an absolute height of the measurement target object based on a refractive index of the measurement target object.

For example, the specific material may include one of metal, plastic and skin, and the measurement target object may be a material having a predetermined viscosity and a predetermined refractive index.

In one embodiment, when a distance between the reference mirror and the measurement target object is shorter than a distance between the light splitting unit and the reference mirror, the processing unit may be configured to turn the calculated shape of the measurement target object upside down with respect to a predetermined base line.

According to the present disclosure, it is possible to effectively measure a three-dimensional shape of a measurement target object using a frequency scanning interferometer. The measurement target object is divided on an area-by-area basis. An absolute height is measured in a first area. A relative height is measured in a second area. The shape of the measurement target object can be calculated by matching the absolute height and the relative height.

Furthermore, even if the measurement target object is a material having a predetermined refractive index, which is formed on metal, plastic, skin or the like, the shape of the measurement target object can be accurately calculated by measuring the absolute height of the measurement target object based on the refractive index thereof.

DETAILED DESCRIPTION

Figure 1:
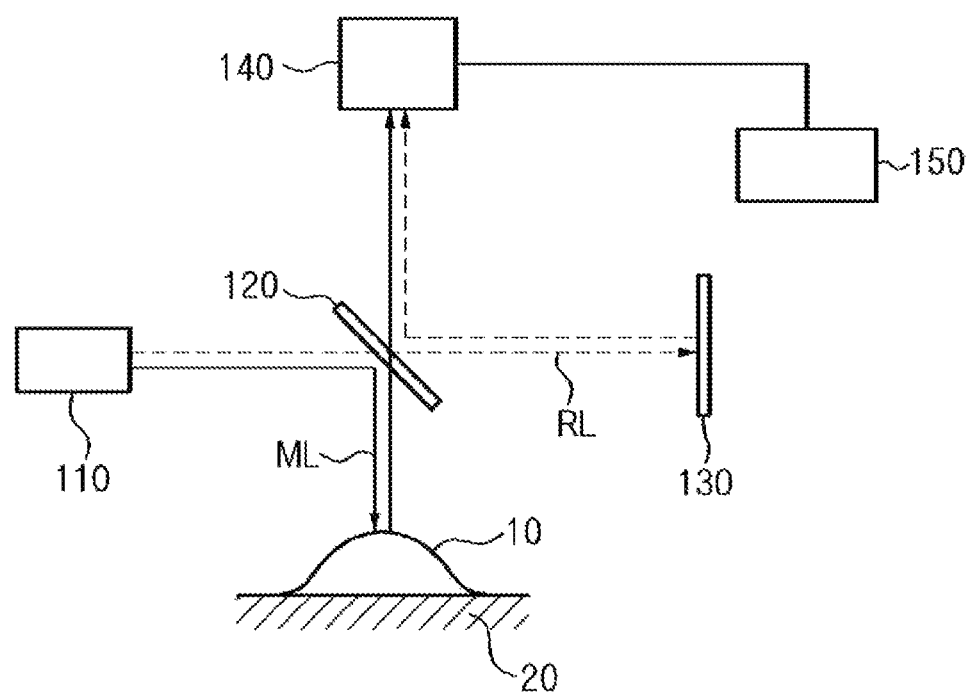
FIG. 1 is a conceptual diagram illustrating a shape measuring device using a frequency scanning interferometer according to one embodiment of the present disclosure.

Embodiments of the present disclosure may be differently modified and may have different forms. Specific embodiments will now be illustrated in the drawings and will be described in detail. However, these are not intended to limit the present disclosure to specific forms disclosed herein. It is to be understood that all the modifications, equivalents and substitutions are included in the idea and technical scope of the present disclosure.

Terms "first" and "second" may be used for describing different components. However, the components shall not be limited by the terms. The terms may be used to distinguish one component from another component. For example, a first component may be named as a second component without departing from the protection scope of the present disclosure. Similarly, a second component may be named as a first component.

The terms used herein are used merely for the purpose of describing specific embodiments and are not intended to limit the present disclosure. A singular expression includes a plural expression unless explicitly mentioned otherwise. In the subject application, it is to be understood that the term "include" or "have" is intended to indicate the existence of a feature, a number, a step, an operation, a component, a part or a combination thereof and is not intended to intentionally exclude the existence or the possibility of addition of one or more features, numbers, steps, operations, components, parts or combinations thereof.

Unless defined otherwise, all the terms used herein, including the technical or scientific terms, have the same meanings as ordinarily understood by a person having an ordinary knowledge in the technical field to which the present disclosure pertains.

The terms ordinarily used and defined in a dictionary shall be interpreted to have the meanings that match with the contextual meanings of the related art. The terms shall not be interpreted in ideal or excessively formal meanings unless explicitly defined otherwise herein.

Preferred embodiments of the present disclosure will now be described in detail with reference to the accompanying drawings.

FIG. 1 is a conceptual diagram illustrating a shape measuring device using a frequency scanning interferometer (FSI) according to one embodiment of the present disclosure.

Referring to FIG. 1, the shape measuring device 100 according to one embodiment includes a light source unit 110, a light splitting unit 120, a reference mirror 130, a light receiving unit 140 and a processing unit 150.

The light source unit 110 may generate light and may change the wavelength of the light.

In one embodiment, the light source unit 110 may include a wavelength-variable laser device, for example, a tunable laser.

For example, the wavelength-variable laser device may generate laser light. The laser light thus generated may have a continuous or discontinuous value within a specific wavelength range.

The light splitting unit 120 splits the light generated from the light source unit 110 into a reference light RL and a measurement light ML.

For example, the light splitting unit 120 may include a beam splitter.

In one embodiment, the light splitting unit 120 transmits at least a portion of the light generated from the light source unit 110. The reference light RL thus transmitted may be provided to the reference mirror 130 which will be described later. Furthermore, the light splitting unit 120 reflects at least a portion of the light generated from the light source unit 110. The measurement light ML thus reflected may be provided toward a measurement target object 10 for which shape measurement is desired.

The reference mirror 130 reflects the reference light RL.

The reference light RL thus reflected may be returned to the light splitting unit 120 and may be reflected toward the light receiving unit 140 which will be described later.

The light receiving unit 140 receives the reference light RL and the measurement light ML.

The reference light RL is reflected by the reference mirror 130 so as to form a reference light path. For example, the reference light path of the reference light RL may be formed in the form indicated by dot line arrows in FIG. 1.

The measurement light ML is reflected by the measurement target object 10 so as to form a measurement light path. For example, the measurement light path of the measurement light ML may be formed in the forms indicated by solid line arrows in FIG. 1.

The measurement target object 10 is formed on a substrate 20 and has a light transmittance. Thus, the measurement light path may be formed by the light being reflected by the measurement target object 10 or may be formed by the light reflected by the substrate 20 after transmitting the measurement target object 10.

For example, the measurement target object 10 may have a viscosity and may have a dot shape when viewed in a plan view.

Figure 2:
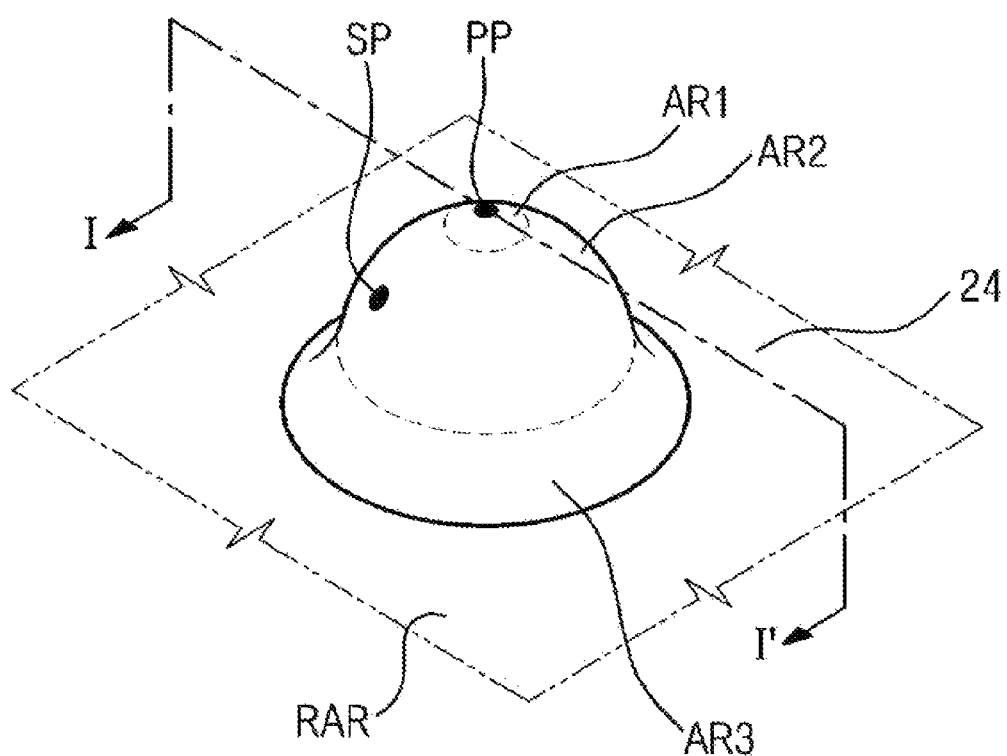
FIG. 2 is a perspective view illustrating one specific example of a measurement target object illustrated in FIG. 1.
Figure 3:
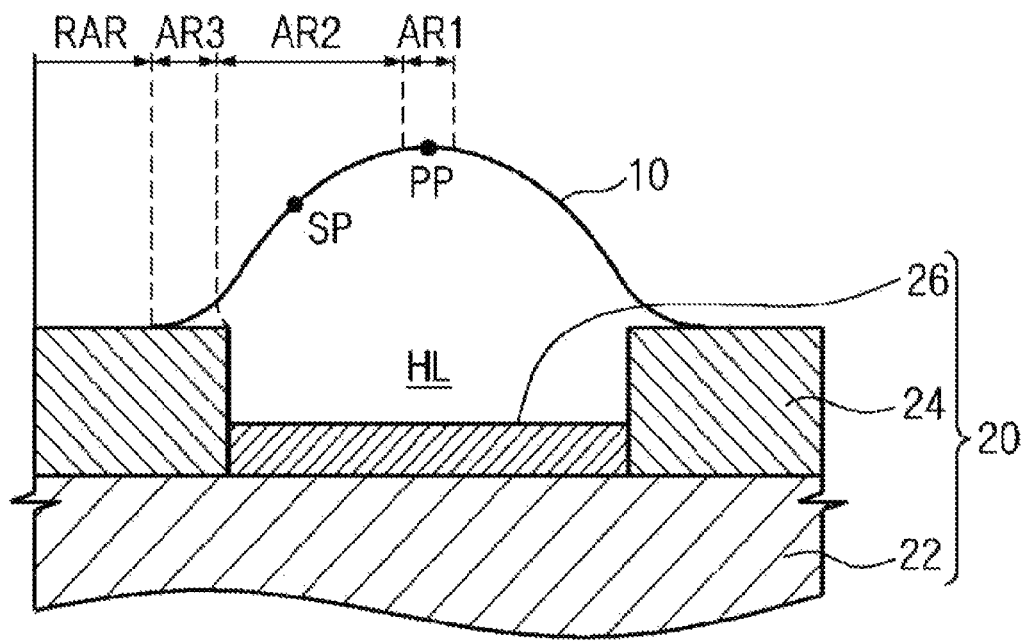
FIG. 3 is a sectional view of the measurement target object taken along the line I-I' in FIG. 2.

FIG. 2 is a perspective view illustrating one specific example of the measurement target object illustrated in FIG. 1. FIG. 3 is a sectional view of the measurement target object taken along the line I-I' in FIG. 2.

Referring to FIGS. 2 and 3, for example, the measurement target object 10 may be formed on the substrate 20 in a shape like a hemisphere, a convex mountain shape or other shapes. The specific shape of the measurement target object 10 may be decided depending on the surface tension and the bonding force of the measurement target object 10.

The substrate 20 may include a base substrate 22, a non-conductive layer 24 formed on the base substrate 22 and provided with at least one hole HL, and a conductive layer 26 formed thinner than the non-conductive layer 24 and corresponding to the hole HL.

For example, the non-conductive layer 24 may include a solder resist. The conductive layer 26 may include copper.

In one embodiment, the measurement target object 10 may include a flux formed at least on the conductive layer 26. The flux may be used for soldering.

The flux formed on the conductive layer 26 may be formed so as to fill at least a portion of the hole HL and may be formed so as to cover a portion of the non-conductive layer 24 which adjoins the hole HL. Furthermore, the flux may be formed so as to fill the entirety of the hole HL and may cover the entirety of the conductive layer 26. In FIGS. 2 and 3, for example, the flux is formed so as to fill the entirety of the hole HL.

The processing unit 150 calculates the shape of the measurement target object based on an interference change between the reference light RL and the measurement light ML which are received by the light receiving unit 140. In this regard, the interference change results from a wavelength change of the light.

The processing unit 150 calculates an absolute height of a first area AR1 of the measurement target object 10 and a relative height of a second area AR2 with respect to the first area AR1 of the measurement target object 10. The processing unit 150 calculates the shape of the measurement target object 10 by matching the absolute height of the first area AR1 and the relative height of the second area AR2.

The first area AR1 may be an area where the light receiving unit 140 can receive the light reflected by the measurement target object 10. The second area AR2 may be an area where the light receiving unit 140 cannot fully receive the light reflected by the measurement target object 10. Furthermore, the first area AR1 and the second area AR2 may be areas where the light receiving unit 140 can receive the light transmitted through the measurement target object 10 and then reflected at the conductive layer 26.

The first area AR1 may include a peak point PP of the measurement target object 10. The second area AR2 may include a plurality of slant points SP positioned in a slant surface around the peak point PP.

The processing unit 150 may calculate the absolute height of the first area using a first light path difference and a second light path difference. The first light path difference is a light path difference between the measurement light ML reflected at the first area of the measurement target object 10 and the measurement light ML reflected at a reference area RAR positioned around the measurement target object 10. The second light path difference is a light path difference between the measurement light ML transmitted through the first area of the measurement target object 10 and then reflected at the conductive layer 26 and the measurement light ML reflected at the reference area RAR.

The reference area RAR is an area which can be set as a reference for calculating the shape of the measurement target object. For example, as illustrated in FIG. 2, the reference area RAR may be an upper surface of the substrate 20.

Figure 4:
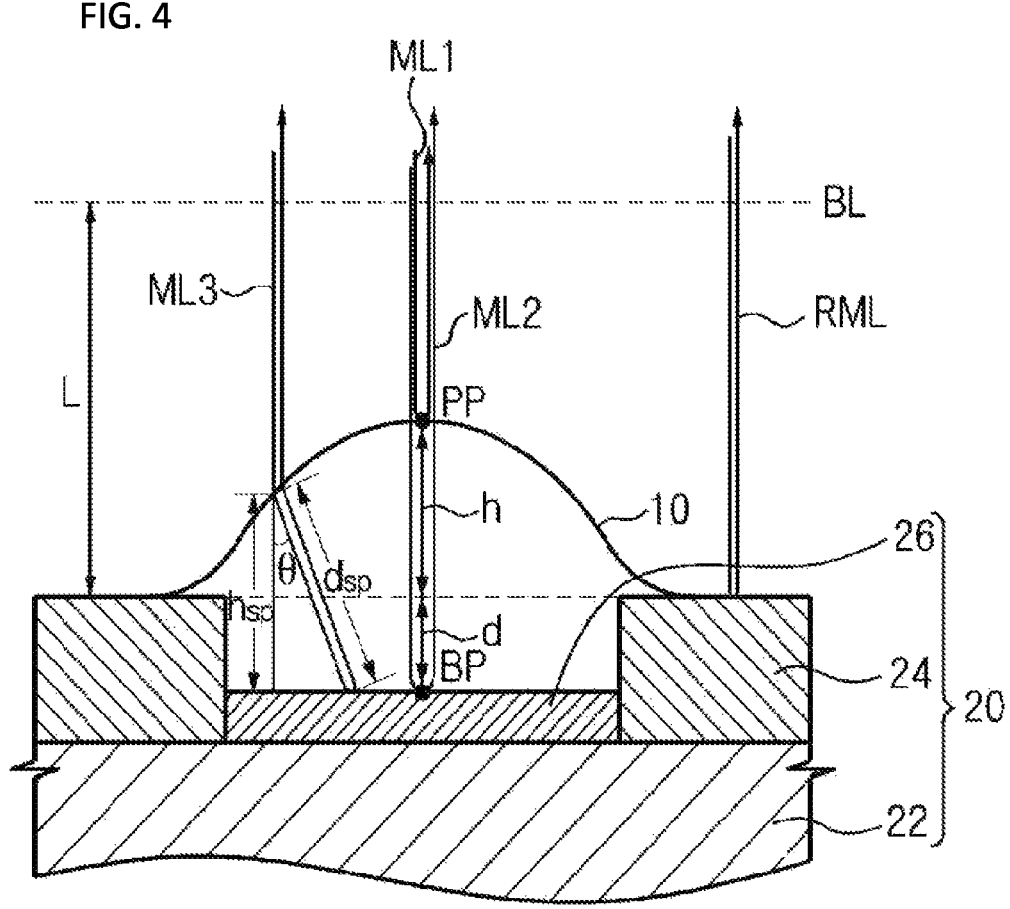
FIG. 4 is a conceptual diagram for explaining a process in which the processing unit illustrated in FIG. 1 calculates the shape of a measurement target object from a behavior of measurement light with respect to the measurement target object.

FIG. 4 is a conceptual diagram for explaining a process in which the processing unit illustrated in FIG. 1 calculates the shape of the measurement target object from a behavior of measurement light with respect to the measurement target object.

Referring to FIG. 4, the measurement light ML may be reflected by the measurement target object 10 in the form of a first measurement light ML1, a second measurement light ML2 and a third measurement light ML3. Furthermore, the measurement light ML may be reflected in a predetermined reference area positioned around the measurement target object 10. As illustrated in FIG. 4, the measurement light ML may be reflected at the upper surface of the substrate 20 in the form of a reference measurement light RML.

The processing unit 150 may measure the shape of the measurement target object 10 using the first, second and third measurement lights ML1, ML2 and ML3 acquired in the light receiving unit 140.

In one embodiment, the processing unit 150 may calculate the absolute height of the first area AR1 using mathematical formulae (1) to (5) which will be described below.

$$O=2L \quad (1)$$

$$O_1'=2(L-h) \quad (2)$$

$$\Delta_1=O-O_1'=2h, h=\Delta_1/2 \quad (3)$$

In the mathematical formulae (1) to (3), O denotes a reference measurement light path, $O_1'$ denotes a first measurement light path, and $\Delta_1$ denotes a first light path difference.

The reference measurement light path is one of the measurement light paths which are formed by the measurement light ML reflected by the measurement target object 10 and which are formed in the forms indicated by solid line arrows in FIG. 1. It suffices that the reference measurement light path is a path fixed and unchanged regardless of the measurement target object 10. In one embodiment, the reference measurement light path is a path formed by the reference measurement light RML illustrated in FIG. 4.

The first measurement light path is one of the measurement light paths which are formed in the forms indicated by solid line arrows illustrated in FIG. 1. The first measurement light path is a path formed by the first measurement light ML1 obtained when the measurement light ML is reflected by the measurement target object 10.

The first light path difference is a light path difference between the reference measurement light path and the first measurement light path and may be acquired by the light receiving unit 140.

As described above, the first measurement light path difference is a difference between light paths. Thus, a common path among the paths along which the measurement light ML moves in the configuration of the optical system illustrated in FIG. 1 may not be considered in the calculation of the first measurement light path difference and may be represented using a predetermined base line BL. For example, the base line BL may be a critical line corresponding to the light path having the same size as the reference light path indicated by dot line arrows in FIG. 1. That is to say, the path of the measurement light ML is larger in size than the reference light path by the distance at which the measurement light ML moves under the base line BL.

Referring to mathematical formula (1), the reference measurement light path may be denoted by 2L which is twice as large as the distance L between the base line BL and the upper surface of the substrate 20.

Referring to mathematical formula (2), the first measurement light ML1 comes back by being reflected by the measurement target object 10. Thus, the first measurement light path may be represented by 2(L−h) which is twice as large as the distance (L−h) between the base line BL and the peak point PP of the measurement target object 10. In this regard, h is the distance between the peak point PP and the upper surface of the substrate 20.

Therefore, referring to mathematical formula (3), the first light path difference may be represented by 2L−2(L−h). It is therefore possible to calculate $h(=\Delta_1/2)$.

Since the reference measurement light path and the first measurement light path are formed in the air without transmitting the measurement target object 10, the advance speed of the light is not reduced by the measurement target object 10. Thus, the light path is not increased under the influence of a refractive index of the measurement target object 10 and may be represented by the actual movement distance of the light.

$$O_2'2(L-h)+2nh+2nd \qquad (4)$$

$$\Delta_2=O-O_2'=2h-2nh-2nh-2nd \qquad (5)$$

$$d=[2h(1-n)-\Delta_2]/2n$$

In mathematical formulae (1), (4) and (5), O denotes a reference measurement light path, $O_2'$ denotes a second measurement light path, and $\Delta_2$ denotes a second light path difference.

The reference measurement light path is the same as described above.

The second measurement light path is one of the measurement light paths which are formed in the forms indicated by solid line arrows in FIG. 1. The second measurement light path is a path formed by the second measurement light ML2 obtained when the measurement light ML is reflected at the conductive layer 26 after transmitting the measurement target object 10.

The second light path difference is a light path difference between the reference measurement light path and the second measurement light path and may be acquired by the light receiving unit 140.

As described above, the second measurement light path difference is a difference between light paths. Thus, a common path among the paths along which the measurement light ML moves in the configuration of the optical system illustrated in FIG. 1 may be neglected in the calculation of the second measurement light path difference and may be represented using a predetermined base line BL. For example, the base line BL may be a critical line corresponding to the light path having the same size as the reference light path indicated by dot line arrows in FIG. 1. That is to say, the path of the measurement light ML is larger in size than the reference light path by the distance at which the measurement light ML moves under the base line BL.

Referring to mathematical formula (1), the reference measurement light path may be denoted by 2L which is twice as large as the distance L between the base line BL and the upper surface of the substrate 20.

Referring to mathematical formula (4), the second measurement light path may be represented by 2(L−h)+2nh+2nd. The second measurement light ML2 comes back by being reflected at the conductive layer 26 after transmitting the measurement target object 10. Thus, the second measurement light ML2 moves twice at the distance (L−h) between the base line BL and the peak point PP of the measurement target object 10, at the distance (h) between the peak point PP and the upper surface of the substrate 20 and at the distance (d) between the upper surface of the substrate 20 and the bottom point BP corresponding to the peak point PP, respectively. At this time, in the first distance, the second measurement light ML2 forms a light path in the air without transmitting the measurement target object 10. Therefore, the light path is represented by L−h. In the second and third distances, the second measurement light ML2 forms light paths within the measurement target object 10 by transmitting the measurement target object 10. Therefore, the light paths are increased just as much as the multiplication of a refractive index n and may be represented by nh and nd, respectively. Accordingly, the second measurement light path is represented by 2(L−h)+2nh+2nd.

Thus, referring to mathematical formula (5), the second light path difference may be represented by 2L−{2(L−h)+2nh+2nd}. It is therefore possible to calculate d(=[2h(1−n)−$\Delta_2$]/2n). In this case, if the measurement target object 10 is a known material, it is possible to easily know the refractive index n from a known physical value. If the measurement target object 10 is not a known material, the refractive index n may be acquired in advance using a sample. It can be noted from mathematical formula (5) that the $\Delta_2$ acquired by the light receiving unit 140 has a negative value. Accordingly, the sign of d is inverted from minus to plus.

As a result, the absolute height of the measurement target object 10 can be acquired by adding h and d using mathematical formulae (3) and (5).

Further, a plurality of measurement target objects 10 may be formed in the form of an array. In this case, when the first light path distance generated by the first measurement light ML1 deviates from a predetermined reference value, it is possible to utilize the d acquired from the adjacent measurement target objects 10. In this case, the height h can be acquired using the d acquired from the adjacent measurement target objects 10, the information on the refractive index n and the mathematical formula (5). The absolute height of the measurement target objects 10 can be acquired by adding h and d.

In one embodiment, the processing unit 150 can calculate the relative height of the second area AR2 using a third light path difference between the measurement light ML, which is reflected at the conductive layer 26 after transmitting the second area AR2 of the measurement target object 10, and the reference light RL.

For example, the processing unit 150 can calculate the relative height of the second area AR2 using mathematical formulae (6) to (8).

$$O_3'=2(L-h_{SP})+2nd_{SP} \qquad (6)$$

$$\Delta_3=O-O_3'=2h_{SP}(1-n/\cos\theta) \qquad (7)$$

$$h_{SP}=\Delta_3/2(1-n/\cos\theta) \qquad (8)$$

$$h_{SP} \propto \Delta_3 \cos\theta/(\cos\theta-n)$$

In mathematical formulae (6) to (8), O denotes a reference measurement light path, $O_3'$ denotes a third measurement light path, and $\Delta_3$ denotes a third light path difference.

The reference measurement light path is the same as described above.

The third measurement light path is one of the measurement light paths which are formed in the forms indicated by solid line arrows in FIG. 1. The third measurement light path is a path formed by the third measurement light ML3 obtained when the measurement light ML is reflected at the conductive layer 26 after transmitting the measurement target object 10 in a refracted state.

The third light path difference is a light path difference between the reference measurement light path and the third measurement light path and may be obtained by the light receiving unit 140.

As described above, the third measurement light path difference is a difference between light paths. Thus, a common path among the paths along which the measurement light ML moves in the configuration of the optical system illustrated in FIG. 1 may not be considered in the calculation of the third measurement light path difference and may be represented using a predetermined base line BL. For example, the base line BL may be a critical line corresponding to the light path having the same size as the reference light path indicated by dot line arrows in FIG. 1. That is to say, the path of the measurement light ML is larger in size than the reference light path by the distance at which the measurement light ML moves under the base line BL.

Referring to mathematical formula (1), the reference measurement light path may be denoted by 2L which is twice as large as the distance L between the base line BL and the upper surface of the substrate 20.

Referring to mathematical formula (6), the third measurement light path may be represented by $2(L-h_{SP})+2nd_{SP}$. The third measurement light ML3 comes back by being reflected at the conductive layer 26 after transmitting the measurement target object 10. Thus, the third measurement light ML3 moves twice at the distance $(L-h_{SP})$ between the base line BL and the slant point SP of the measurement target object 10 and at the refracted distance $d_{SP}$ between the slant point SP and the conductive layer 26, respectively. At this time, in the first distance, the third measurement light ML3 forms a light path in the air without transmitting the measurement target object 10. Therefore, the light path is represented by $L-h_{SP}$. In the second distance, the third measurement light ML3 forms a light path within the measurement target object 10 by transmitting the measurement target object 10. Therefore, the light path is increased just as much as the multiplication of a refractive index n and may be represented by $nd_{SP}$. Accordingly, the third measurement light path is represented by $2(L-h_{SP})+2nd_{SP}$.

Therefore, referring to mathematical formula (7), $D_{SP}$ is $h_{SP}/\cos\theta$. Thus, the third light path difference may be represented by $2h_{SP}(1-n/\cos\theta)$.

Referring to mathematical formula (8), $h_{Sp}$ may be represented by $\Delta_3/2(1-n/\cos\theta)$. Thus, it can be noted that $h_{SP}$ is proportional to $\Delta_3 \cos\theta/(\cos\theta-n)$.

Since $\theta$ is not largely changed depending on the position of the slant point SP, the absolute height $h_{SP}$ is substantially proportional to $\Delta_3$. Consequently, the relative heights of a plurality of slant points SP may be determined by $\Delta_3$ acquired by the light receiving unit 140. That is to say, if the relative heights of the slant points SP are matched on the basis of the already-acquired peak point PP of the first area AR1, it is possible to acquire a height profile of the second area AR2.

Referring to mathematical formula (7), it can be noted that $\Delta_3$ acquired by the light receiving unit 140 has a negative value. Accordingly, prior to the matching, the sign of the vales of $\Delta_3$ with respect to the slant points SP is inverted from minus to plus.

Referring again to FIGS. 1 to 3, the processing unit 150 can calculate the predicted height of a third area AR3 of the measurement target object 10. Thus, the shape of the measurement target object 10 can be calculated using the absolute height of the first area AR1, the relative height of the second area AR2 and the predicted height of the third area AR3.

Specifically, the processing unit 150 can calculate the predicted height of the third area AR3 by setting the third area AR3 using the relative height of the second area AR2 and predicting the height distribution of the third area AR3 based on the height distribution of the second area AR2.

The third area AR3 is an area that does not receive the light reflected by the measurement target object 10. After transmitting the measurement target object 10, the measurement light ML fails to reach the conductive layer 26 due to the existence of the non-conductive layer 24. Thus, the light reflected at the conductive layer 26 is also not received in the third area AR3. Accordingly, the third area AR3 may be set as an area that does not receive the measurement light ML or as points that discontinuously indicate an inner boundary and an outer boundary of the third area AR3.

As an alternative example, the outer boundary of the third area AR3 may be derived from a two-dimensional plane image taken from above the measurement target object 10. That is to say, the plane shape of the measurement target object 10 appears in the two-dimensional plane image. It is therefore possible to set the outer boundary of the third area AR3.

After the third area AR3 is set in this way, the height of the inner boundary of the third area AR3 may be set to become equal to the height of the second area AR2. The height of the outer boundary of the third area AR3 may be set to become equal to 0.

Next, the processing unit 150 can calculate the predicted height of the third area AR3 by applying an extrapolation method based on the height information of the second area AR2. The height information of the second area AR2 is the information on the absolute height of the second area AR2 calculated by matching the relative height of the second area AR2 and the absolute height of the first area AR1 as described earlier.

Alternatively, the processing unit 150 may calculate the height distribution of the third area AR3 between the inner boundary and the outer boundary by assuming the height distribution of the third area AR3 to be linear. This is because the range of the third area AR3 is not large and because the volume of the measurement target object 10 corresponding to the third area AR3 is not large as compared with the entire volume.

As described above, the processing unit 150 can calculate the heights of the first area AR1, the second area AR2 and the third area AR3. It is therefore possible to measure the height-based three-dimensional shape of the measurement target object 10.

Figure 5:
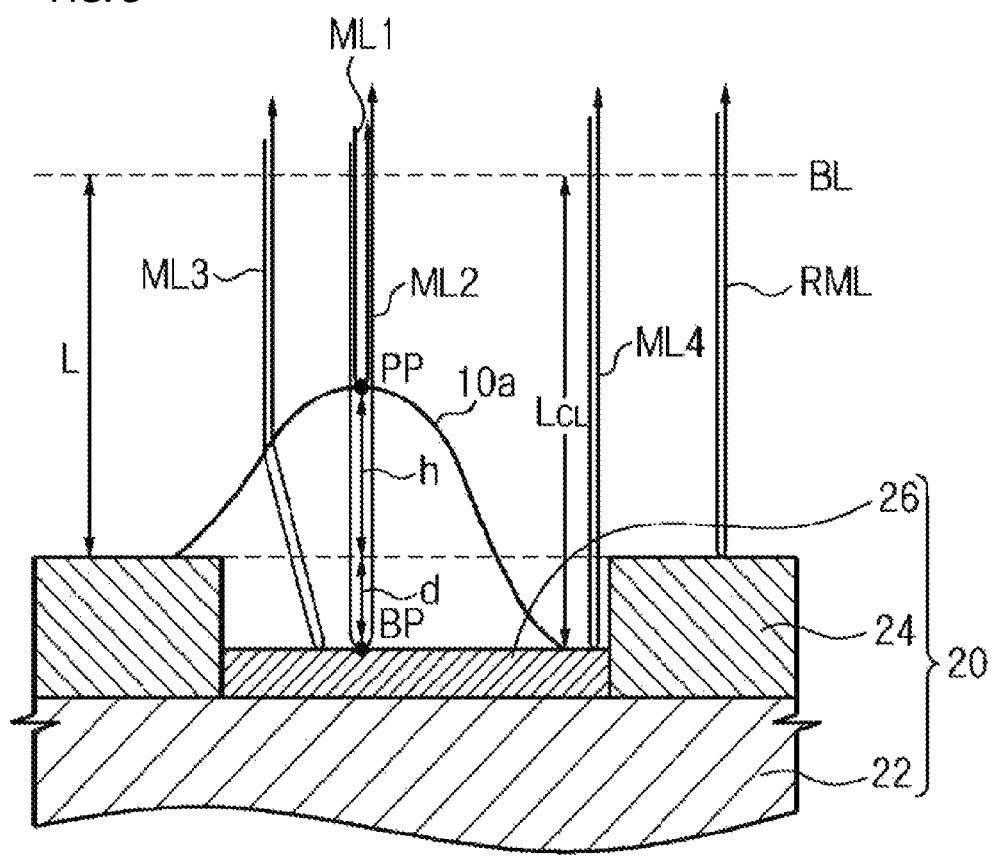
FIG. 5 is a conceptual diagram for explaining a process in which the processing unit illustrated in FIG. 1 calculates the shape of another measurement target object from a behavior of measurement light with respect to another measurement target object.

FIG. 5 is a conceptual diagram for explaining a process in which the processing unit illustrated in FIG. 1 calculates the shape of another measurement target object from a behavior of the measurement light with respect to another measurement target object.

Referring to FIG. 5, the measurement target object 10a is not formed so as to fill the entirety of the hole HL but is formed so as to fill a portion of the hole HL. A portion of the measurement target object 10a is formed so as to cover a portion of the non-conductive layer 24 that adjoins the hole HL.

As illustrated in FIGS. 2 to 4, the measurement light ML may be reflected by the measurement target object 10a in the form of the first measurement light ML1, the second measurement light ML2 and the third measurement light ML3. Furthermore, the measurement light ML may be reflected in a predetermined reference area positioned around the measurement target object 10a. As illustrated in FIG. 4, the measurement light ML may be reflected by the upper surface of the substrate 20 in the form of the reference measurement light RML. In addition, the measurement light ML may be reflected in a portion of the hole HL not filled by the measurement target object 10a, namely in an exposed portion of the conductive layer 26, in the form of fourth measurement light ML4.

The process in which the processing unit 150 measures the shape of the measurement target object 10a using the first, second and third measurement lights ML1, ML2 and ML3 acquired in the light receiving unit 140 is substantially identical with the process described with reference to FIG. 4. Therefore, repetitive descriptions are omitted herein. Unlike the configuration illustrated in FIG. 4, a portion of the measurement target object 10a does not cover the non-conductive layer 24. The area of the measurement target object 10a corresponding thereto (the end portion of a right slant surface of the measurement target object 10a in FIG. 5) does not correspond to the third area AR3 but corresponds to the second area AR2.

Referring to FIG. 5, the processing unit 150 can measure the absolute height of the conductive layer 26 exposed in the vicinity of the measurement target object 10a using the fourth measurement light ML4 acquired by the light receiving unit 140. Specifically, the processing unit 150 can measure the absolute height of the conductive layer 26 using the following mathematical formulae (9) and (10) similar to mathematical formula (3) described above.

$$O_4'=2(L-L_{CL}) \quad (9)$$

$$\Delta_4=O-O_4'=2L_{CL}, L_{CL}=\Delta_4/2 \quad (10)$$

In mathematical formulae (9) and (10), O denotes a reference measurement light path, $O_4'$ denotes a fourth measurement light path, and $\Delta_4$ denotes a fourth light path difference.

The reference measurement light path is the same as described above.

The fourth measurement light path is one of the measurement light paths which are formed in the forms indicated by solid line arrows in FIG. 1. The fourth measurement light path is a path formed by the fourth measurement light ML4 obtained when the measurement light ML is reflected at the conductive layer 26.

The fourth light path difference is a light path difference between the reference measurement light path and the fourth measurement light path and may be obtained by the light receiving unit 140.

Using mathematical formulae (9) and (10), the distance $L_{CL}$ between the base line BL and the upper surface of the conductive layer 26 can be found in the same method as the method of finding h described above.

As described above, the processing unit 150 can calculate the heights of the first area AR1, the second area AR2 and the third area AR3. It is therefore possible to measure the height-based three-dimensional shape of the measurement target object 10.

According to the shape measuring device described above, it is possible to effectively measure the three-dimensional shape of the measurement target object using a frequency scanning interferometer. The measurement target object is divided on an area-by-area basis. The absolute height is measured in the first area. The relative height is measured in the second area. The shape of the measurement target object can be calculated by matching the absolute height and the relative height.

In the embodiment described above, the shape of the measurement target object 10 is measured in a state in which the measurement target object 10 is formed on the substrate 20 including both the non-conductive layer 24 and the conductive layer 26. As an alternative embodiment, shape measurement may be performed in the case where a measurement target object is formed on a surface of a specific material. It goes without saying that not only a flux but also all kinds of materials having a predetermined refractive index can be used as the measurement target object 10. The shape measuring device may be suitably used to measure the shape of a liquid phase material having a specified viscosity and a specified transmittance.

The specific material used herein may be, but is not limited to, metal, plastic, skin or the like having an irregular reflection property. In the case where the shape of the measurement target object formed on the surface of the specific material is measured using a frequency scanning interferometer, the height of the shape of the measurement target object may be measured as a negative value due to the characteristics of the frequency scanning interferometer. That is to say, depending on the refractive index of the measurement target object, the measurement target object may look upside down as if the measurement target object is positioned more inward than a reference point or a reference line on the surface of the specific material.

Specifically, when the distance between the reference mirror and the measurement target object is shorter than the distance between the light splitting unit and the reference mirror, the measurement target object looks upside down with reference to the reference line. Where the distance between the reference mirror and the measurement target object is larger than the distance between the light splitting unit and the reference mirror, it is possible to derive a shape having a predetermined height.

In this regard, when the measurement target object is turned upside down with respect to a preset reference point, it is necessary to perform turning-upside-down again in order to obtain a normal shape. That is to say, as the turning-upside-down method, it may be possible to use a method in which, where the shape height is measured as a negative value, the shape height is multiplied by a minus sign or is converted to an absolute value (e.g., |h|). Thus, regardless of the distance between the reference mirror and the measurement target object, the shape of the measurement target object can be displayed by a positive value height with respect to the base line.

Accordingly, if calculation is performed except the d value (the term 2nd) from mathematical formulae (4) and (5), it is possible to know the absolute height h of the measurement target object. If the method described above with reference to FIGS. 1 to 5 is used based on the absolute height of the measurement target object, it is possible to measure the shape of the entire measurement target object.

According to the shape measuring device described above, even if the measurement target object is a material having a predetermined refractive index, which is formed on metal, plastic, skin or the like, the shape of the measurement target object can be accurately calculated by measuring the absolute height of the measurement target object based on the refractive index thereof.

While preferred embodiments of the present disclosure have been described above, it will be understood by a person skilled in the art that embodiments of the present disclosure may be changed and modified in many different forms without departing from the idea and scope of the present disclosure defined in the appended claims. Accordingly, the foregoing descriptions and the accompanying drawings shall be construed as illustrating embodiments of the present disclosure and not to limiting the technical concept.

What is claimed is:
1. A shape measuring device, comprising:
  a light source unit configured to generate a light and change a wavelength of the light;
  a light splitting unit configured to split the light generated from the light source unit into at least a reference light and a measurement light;
  a reference mirror configured to reflect the reference light;

a light receiving unit configured to receive the reference light reflected by the reference mirror so as to form a reference light path and to receive the measurement light reflected by a measurement target object formed on a material having an irregular reflection property so as to form a measurement light path, the measurement target object being formed in a lumpy shape with a peak point and a slant surface, and the measurement target object including a first area having the peak point, and a second area having at least a portion of the slant surface; and a processing unit configured to calculate a relative height of the second area based on a first light path difference between a reference measurement light path and a first measurement light path and to calculate a shape of the measurement target object based on the relative height of the second area, wherein the reference measurement light path is formed by a reference measurement light, wherein the reference measurement light is reflected at an exposed portion of an upper surface of the material, wherein the first measurement light path is formed by a first measurement light, wherein the first measurement light is refractively transmitted through the second area of the measurement target object along an incidence path, irregularly reflected at a covered portion of the upper surface of the material, and then returned backward through the incidence path, and wherein the covered portion is covered with the measurement target object.

2. The shape measuring device of claim 1, wherein the material comprises a substrate including a base substrate, a non-conductive layer having the exposed portion, and a conductive layer having the covered portion, and wherein the processing unit is configured:

to calculate an absolute height of the first area based on a second light path difference between the reference measurement light path and a second measurement light path and a third light path difference between the reference measurement light path and a third measurement light path; and to calculate the shape of the measurement target object by matching the absolute height of the first area and the relative height of the second area, wherein the second measurement light path is formed by a second measurement light, wherein the second measurement light is reflected at the first area of the measurement target object, wherein the third measurement light path is formed by a third measurement light, and wherein the third measurement is transmitted through the first area of the measurement target object, and reflected at the covered portion.

3. A shape measuring method in a frequency scanning interferometer including a light source unit capable of changing a wavelength of a light, a reference mirror, a beam splitter, a light receiving unit and a processing unit, the shape measuring method comprising:

splitting, by the reference mirror, the light generated from the light source unit into a first light having a first light path;

splitting, by the beam splitter, the light generated from the light source unit into a second light different from the first light and having a second light path, by the second light being reflected by a measurement target object formed on a material having an irregular reflection property, the measurement target object being formed in a lumpy shape with a peak point and a slant surface, and the measurement target object including a first area having the peak point, and a second area having at least a portion of the slant surface;

calculating, by the processing unit, a relative height of the second area based on a first light path difference between a reference measurement light path and a first measurement light path; and calculating, by the processing unit, a shape of the measurement target object based on the relative height of the second area, wherein the reference measurement light path is formed by a reference measurement light, wherein the reference measurement light is reflected at an exposed portion of an upper surface of the material, wherein the exposed portion is not covered with the measurement target object, wherein the first measurement light path is formed by a first measurement light, wherein the first measurement light is refractively transmitted through the second area of the measurement target object along an incidence path, irregularly reflected at a covered portion of the upper surface of the material, and then returned backward through the incidence path; and wherein the covered portion is covered with the measurement target object.

4. The shape measuring method of claim 3, wherein calculating the shape of the measurement target object comprises:

calculating, by the processing unit, an absolute height of the first area based on a second light path difference between the reference measurement light path and a second measurement light path a third light path difference between the reference measurement light path and a third measurement light path; and calculating, by the processing unit, the shape of the measurement target object by matching the absolute height of the first area and the relative height of the second area, wherein the second measurement light path is formed by a second measurement light, wherein the second measurement light is reflected at the first area of the measurement target object, wherein the third measurement light path is formed by a third measurement light, and wherein the third measurement light is transmitted through the first area of the measurement target object and reflected at the covered portion.

5. A shape measuring device, comprising:

a light source unit configured to generate a light and change a wavelength of the light;

a first light path changing unit configured to enable a first light, which is a portion of the light generated from the light source unit, to have a first light path;

a second light path changing unit configured to enable a second light, which is at least a portion of the light generated from the light source unit and is different from the first light, to have a second light path by being reflected by a measurement target object formed on a material having an irregular reflection property, the measurement target object being formed in a lumpy shape with a peak point and a slant surface, and the measurement target object including a first area including the peak point, and a second area including at least a portion of the slant surface;

a light receiving unit configured to receive the first light passing through the first light path and the second light passing through the second light path; and a processing unit configured to calculate a relative height of the second area based on a first light path difference between a reference measurement light path and a first measurement light path, and to calculate a shape of the measurement target object based on the relative height of the second area, wherein the reference measurement light path is formed by a reference measurement light, wherein the reference measurement light is reflected at an exposed portion of an upper surface of the material, wherein the first measurement light path is formed by a first measurement light, wherein the first measurement light is refractively transmitted through the second area of the measurement target object along an incidence path, irregularly reflected at a covered portion of the upper surface of the material, and then returned backward through the incidence path, and wherein the covered portion is covered with the measurement target object.

6. The shape measuring device of claim 5, wherein the material comprises a substrate including a base substrate, a non-conductive layer having the exposed portion, and a conductive layer having the covered portion, and wherein the processing unit is configured:

to calculate an absolute height of the first area based on a second light path difference between the reference measurement light path and a second measurement light path, and a third light path difference between the reference measurement light path and a third measurement light path, and to calculate the shape of the measurement target object by matching the absolute height of the first area and the relative height of the second area, wherein the second measurement light path is formed by a second measurement light, wherein the second measurement light is reflected at the first area of the measurement target object, wherein the third measurement light path is formed by a third measurement light, and wherein the third measurement Light is transmitted through the first area of the measurement target object and reflected at the covered portion.

\* \* \* \* \*